US00PP16331P3

(12) United States Plant Patent
Larsen

(10) Patent No.: US PP16,331 P3
(45) Date of Patent: Mar. 14, 2006

(54) *OSTEOSPERMUM* PLANT NAMED 'SUNNY STEPHANIE'

(50) Latin Name: *Osteospermum ecklonis (DC) T. Norl.*
Varietal Denomination: Sunny Stephanie

(75) Inventor: Bjarne N. Larsen, Odense N (DK)

(73) Assignee: Sunny Gronnegyden APS, Odense N (DK)

( * ) Notice: Subject to any disclaimer, the term of this patent is extended or adjusted under 35 U.S.C. 154(b) by 116 days.

(21) Appl. No.: 10/788,299

(22) Filed: Mar. 1, 2004

(65) Prior Publication Data

US 2005/0193457 P1 Sep. 1, 2005

(51) Int. Cl.
*A01H 5/00* (2006.01)

(52) U.S. Cl. ..... Plt./360

(58) Field of Classification Search ..... Plt./360
See application file for complete search history.

(56) References Cited

PUBLICATIONS

GTITM UPOVROM Citation for 'Sunny Stephanie' as per QZ PBR 020998; Jul. 3, 2002.*

* cited by examiner

*Primary Examiner*—Kent Bell
(74) *Attorney, Agent, or Firm*—Foley & Lardner, LLP

(57) ABSTRACT

A new distinct cultivar of *Osteospermum* plant named 'Sunny Stephanie', characterized by purple ray floret color from RHS N78A with stripes of RHS N77B purple to RHS 59C, red-purple, with stripes of RHS N57B red-purple; dense and bushy plant form, mainly due to more upright stems; moderately vigorous growth habit, less need for chemical growth retardation; and high number of inflorescences per plant.

4 Drawing Sheets

Genus and species of the plant claimed: *Osteospermum ecklonis* (DC) T. Norl.
Variety denomination: 'Sunny Stephanie'.

BACKGROUND OF THE INVENTION

The present Invention relates to a new and distinct cultivar of *Osteospermum* plant, botanically known as *Osteospermum ecklonis* (DC) T. Norl., commonly known by the name Cape Daisy and hereinafter referred to by the name 'Sunny Stephanie'.

The new *Osteospermum* is a product of a planned breeding program conducted by the Inventor, Bjarne N. Larsen, in Stige, Denmark. The new *Osteospermum* originated from a cross made in 1999 between *Osteospermum ecklonis* (DC) T. Norl. variety named 'Sunny Martha' (unpatented) and *Osteospermum ecklonis* (DC) T. Norl. designated '2.223.98' (unpatented). The Inventor selected the new *Osteospermum* cultivar from the progeny of the above crossing in 2002 on the basis of its inflorescence color and compact, freely branching habit. Plants of the new *Osteospermum* are upright, compact and have a unique color combination of upper and underside of the rayflorets.

Asexual reproduction of the new cultivar by terminal vegetative cuttings taken and propagated during trial production batches in Stige, Denmark, has shown that the unique features of this new *Osteospermum* are stable and reproduced true to type in many successive generations.

BRIEF SUMMARY OF THE INVENTION

Plants of the cultivar 'Sunny Stephanie' have not been observed under all possible environmental conditions. The phenotype may vary somewhat with variations in environment such as temperature, light intensity, day length, and fertility level without, however, any variance in genotype.

The following traits have been repeatedly observed and are determined to be the unique characteristics of 'Sunny Stephanie'. These characteristics in combination distinguish 'Sunny Stephanie' as a new and distinct cultivar:

1. Purple ray floret color from RHS N78A with stripes of RHS N77B, purple, to RHS 59C, red-purple with stripes of RHS N57B, red-purple.
2. Dense and bushy plant form, mainly due to more upright stems.
3. Moderately vigorous growth habit, less need for chemical growth retardation.
4. High number of inflorescences per plant.

Plants of the cultivar 'Sunny Stephanie' can be compared to plants of the parental cultivars 'Sunny Martha' and '2.223.98'. Plants of the cultivar 'Sunny Stephanie' differ from plants of the parental cultivars, 'Sunny Martha' and '2.223.98', primarily in inflorescence color.

Plants of the cultivar 'Sunny Stephanie' can be compared to plants of the *Osteospermum ecklonis* (DC) T. Norl. Cultivar 'Sunny Nathalie' (U.S. Plant Pat. No. 13,358). In side-by-side comparisons conducted by the Inventor in Stige Denmark, plants of the cultivar 'Sunny Stephanie' and 'Sunny Nathalie' differ in the following characteristics:

1. 'Sunny Stephanie' has striking color combinations of purple to red-purple ray florets and dark purple disk florets with orange pollen.
2. 'Sunny Stephanie' has yellow-green-colored leaves while plants of the cultivar 'Sunny Nathalie' have darker green leaves.
3. 'Sunny Stephanie' has shorter and sturdier peduncles than plants of the cultivar 'Sunny Nathalie'.
4. 'Sunny Stephanie' is shorter and more compact than the plants of the cultivar 'Sunny Nathalie'.
5. 'Sunny Stephanie' has more and larger inflorescences per plant than the plants of the cultivar 'Sunny Nathalie'.

Plants of the cultivar 'Sunny Stephanie' can be compared to plants of the *Osteopermum ecklonis* (DC) T. Norl. cultivar 'Sunny Ingrid' (U.S. Plant Pat. No. 10,996). The following table shows a side-by-side comparison conducted by the Inventor in Stige, Denmark, between 'Sunny Stephanie' and 'Sunny Ingrid'.

TABLE 1

| Characteristic | 'Sunny Stephanie' | 'Sunny Ingrid' |
|---|---|---|
| Plant Height | 20 cm | 40 cm |
| Inflorescence Diameter | 5 cm | 6 cm |
| Ray floret Color (upper surface) | Purple, N78A to red-purple 59C, with brownish purple stripes, N77B to N57B | Purple, 80A |
| Peduncle Length | 5 cm | 14 cm |

BRIEF DESCRIPTION OF THE PHOTOGRAPHS

The accompanying colored photographs illustrate the overall appearance of the new *Osteospermum* cultivar 'Sunny Stephanie' showing the colors as true as is reasonably possible with colored reproductions of this type. Colors in the photographs may differ slightly from the color values cited in the detailed botanical description which accurately describe the color of the new *Osteospermum* cultivar 'Sunny Stephanie'.

The first photograph comprises a side perspective view of a typical flowering plant of 'Sunny Stephanie' as grown in an 11 cm pot.

The second photograph is a close-up of the young and older inflorescences of 'Sunny Stephanie'.

The third photograph is a top view of a typical flowering plant of 'Sunny Stephanie'.

The fourth photograph shows the inflorescences and leaves of 'Sunny Stephanie' (in the fourth photograph, 'Sunny Stephanie' is labelled by its breeder's reference no. 50.037.00).

DETAILED BOTANICAL DESCRIPTION

In the following description, color references are made to The Royal Horticultural Society Colour Chart, 4$^{th}$ edition, where general terms of ordinary dictionary significance are used. Plants were grown under greenhouse conditions. The plants described were grown for about 20 weeks after cutting.

Plant description:

*Form.*—Perennial plant with upright plant habit; composite head flowers; freely branching with lateral flowering branches forming at every node; dense and bushy.

*Crop time.*—After rooting, about 18 weeks are required to produce finished flowering plants in 11 cm pots.

*Plant height* (*soil level to top of plant plane*).—About 20 cm.

*Plant width* (*diameter*).—Typical: 18 cm. Observed: 17–20 cm.

*Vigor.*—Moderately vigorous growth rate.

*TIme to initiate roots.*—About 10 to 14 days at 18 to 21° C. in tunnels in a greenhouse.

*Root description.*—Fine, well branched.

*Foliage description.*—Leaves alternate, single, pinnate venation. Length: 4–7 cm. Width: About 30 mm. Shape: Obovate. Apex: obtuse. Base: attenuate. Margin: broadly dentate. Texture: smooth, glabrous, shiny. Scattered short, stiff hairs. Color: Young foliage, upper and lower surfaces: RHS 147B, yellow-green. Mature foliage, upper surface RHS N147A; lower surface RHS 148A, yellow-green. Venation, RHS 148A.

Inflorescence description:

*Inflorescence arrangement and shape.*—Tubular disk and ray florets in composite daisy heads; with 15 parted involucre; inflorescence diameter: 4–6 cm; sturdy peduncles.

*Natural flowering season.*—Continuous throughout the spring and summer. Season can be extended by vernalization and long day treatments.

*Inflorescence longevity on the plant.*—Longevity of individual inflorescences is highly dependent on temperature and light conditions 5 to 6 days. Inflorescences persistent, ray florets folding and withering slowly.

*Inflorescence diameter.*—About 5 cm.

*Inflorescence depth.*—Typical: 6 mm. Observed: composite head 6 mm.

*Inflorescences.*—Ray Florets: Typical number of ray florets per inflorescence: 17. Observed number of ray florets per inflorescence: 15–18. Length: Ray petals: About 27 mm. Width (diameter): About 8 mm. Ray floret apex: lanceolate, acute. Ray floret base: attenuate. Ray floret margin: entire. Ray floret color: Upper surfaces, purple RHS N78A with stripes of purple, RHS N77B, to red-purple, RHS 59C with stripes of RHS N57B, red-purple.

*Disk florets.*—Typical number of disks florets per inflorescence: 60. Observed number of disks florets per inflorescence: 50–70. Length: Disk florets: About 6 mm. Width (diameter): About 3 mm. Disk floret overall shape: tubular. Disk floret apex: attenuate. Disk floret base: fused. Disk floret margin: entire. Disk floret color: RHS79B, dark purple.

*Peduncle.*—Strength: Moderately strong. Length: About 5 cm. Diameter: About 3 mm. Color: 144C yellow-green.

*Phyllary.*—Typical number of phyllaries: 15. Observed number of phyllaries: 12–16. Length: 6–12 mm. Width: 1–3. Overall shape: lanceolate. Apex shape: accuminate. Base shape: fused. Margin: entire. Color: Upper surface: RHS 137D, green; lower surface: RHS 137D, green.

Reproductive organs:

*Androecium.*—Location: disc florets only.Anthers: Linear fused, stamen color RHS 202A, black. Pollen: RHS 26A, Orange.

*Gynoecium.*—Location of gynoecium: ray and disc florets. Pistil and stigma: Typical pistil number: 1. Observed pistil number: 1. Stigma color: RHS 16C, yellow-orange. Seed: Length: About 1 mm. Diameter: About 0.3 mm.

Disease/pest resistance: Good.

Disease/pest susceptibility: Low.

Weather tolerance: Plants of the new *Osteospermum* have exhibited good tolerance to draught, rain and wind, temperature down to −1° C. (30° F.).

I claim:

1. A new and distinct cultivar of *Osteospermum* plant named 'Sunny Stephanie', as illustrated and described herein.

* * * * *

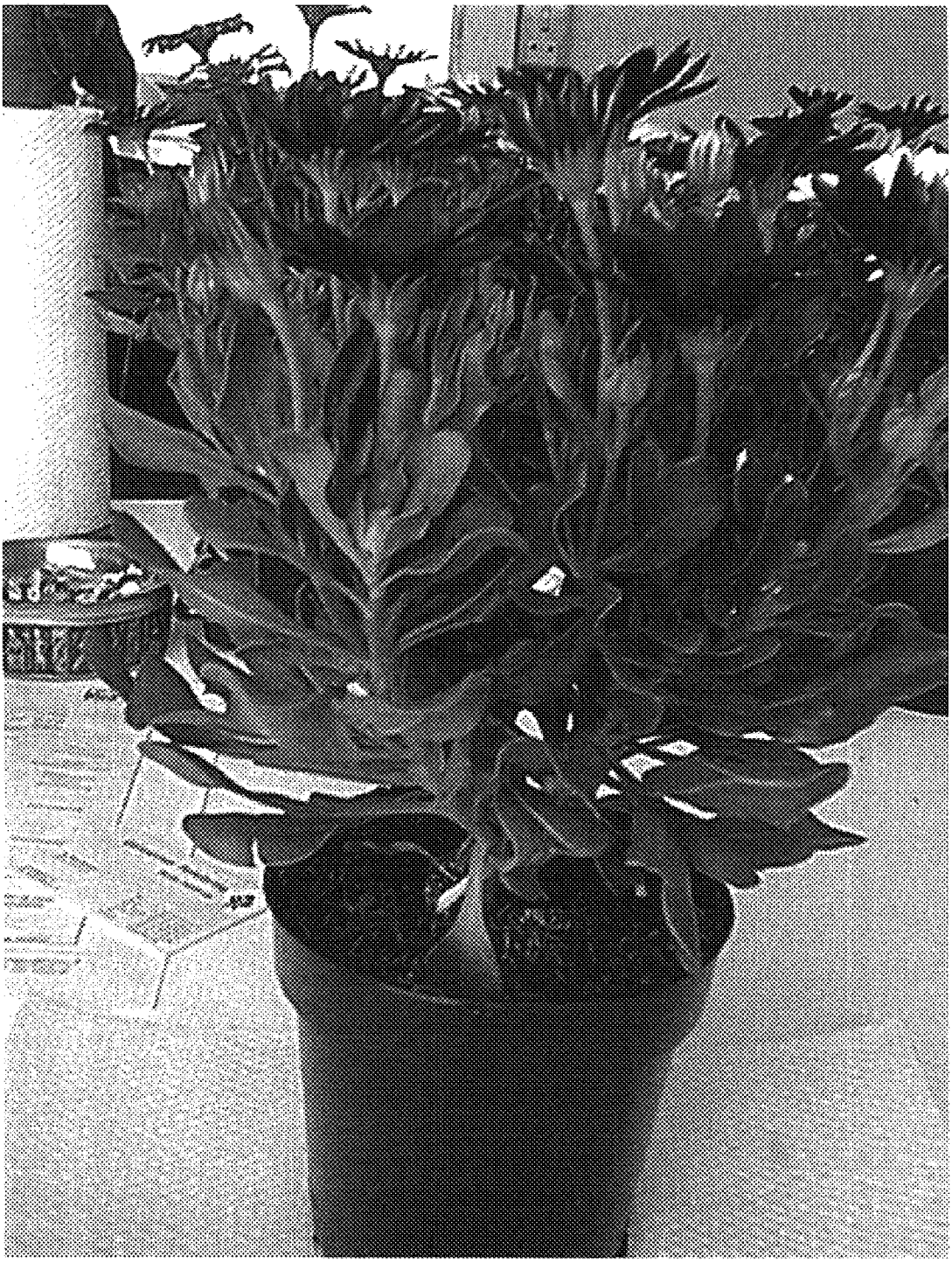

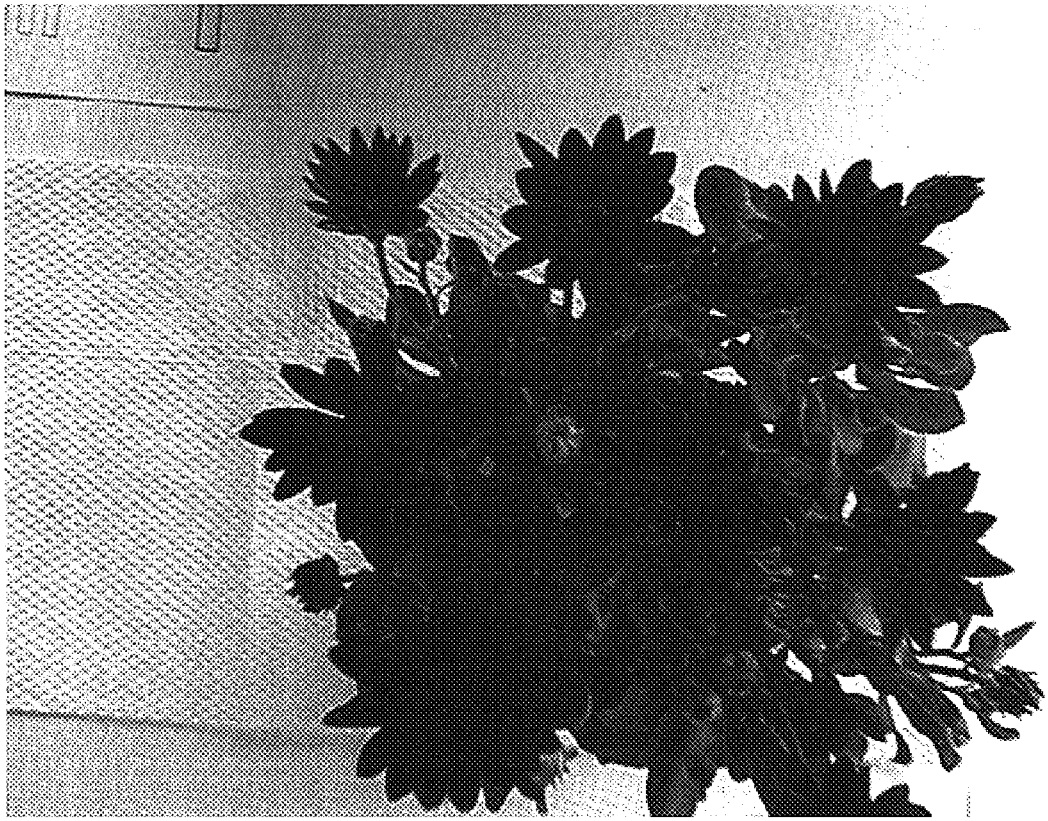

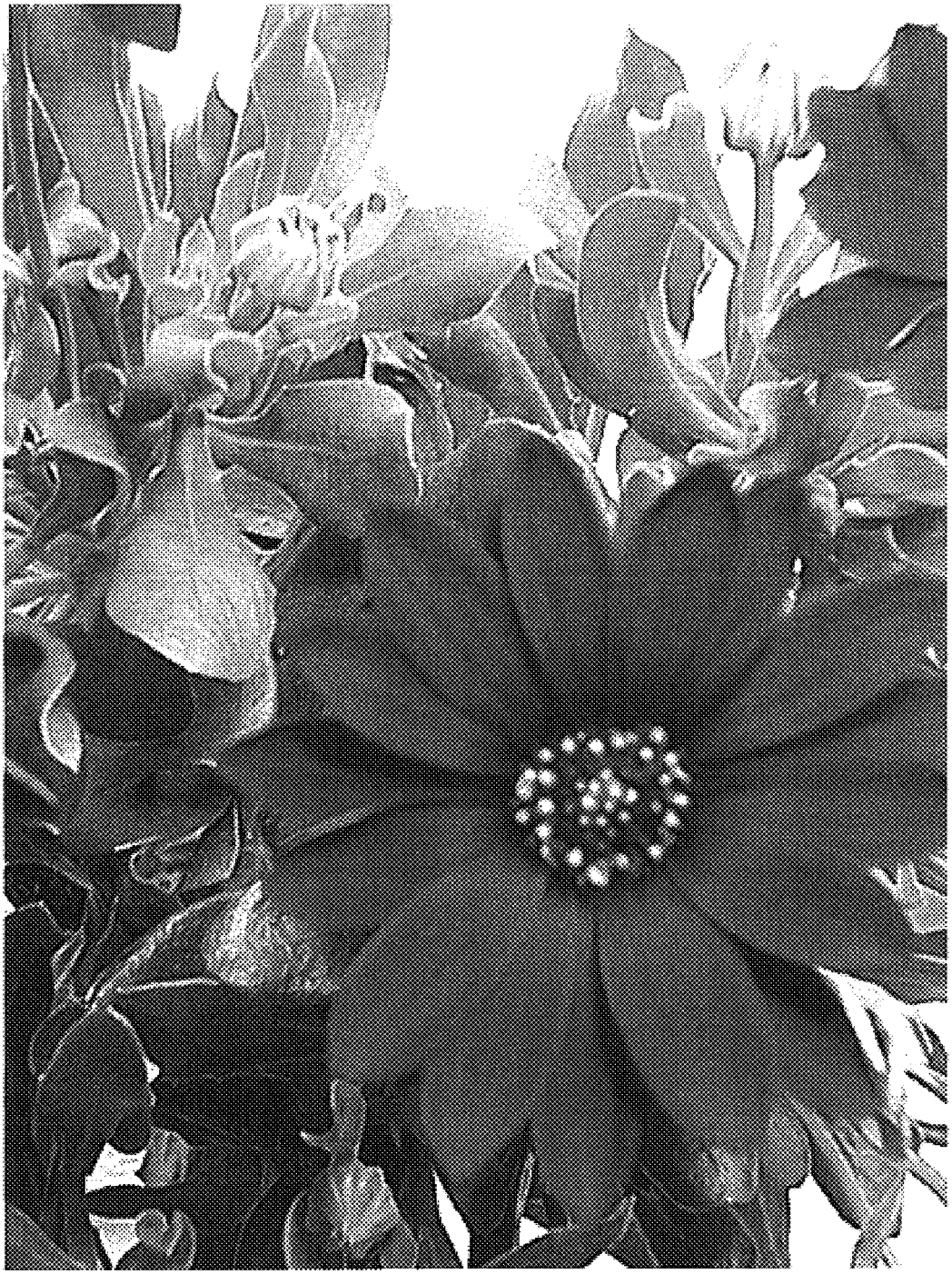

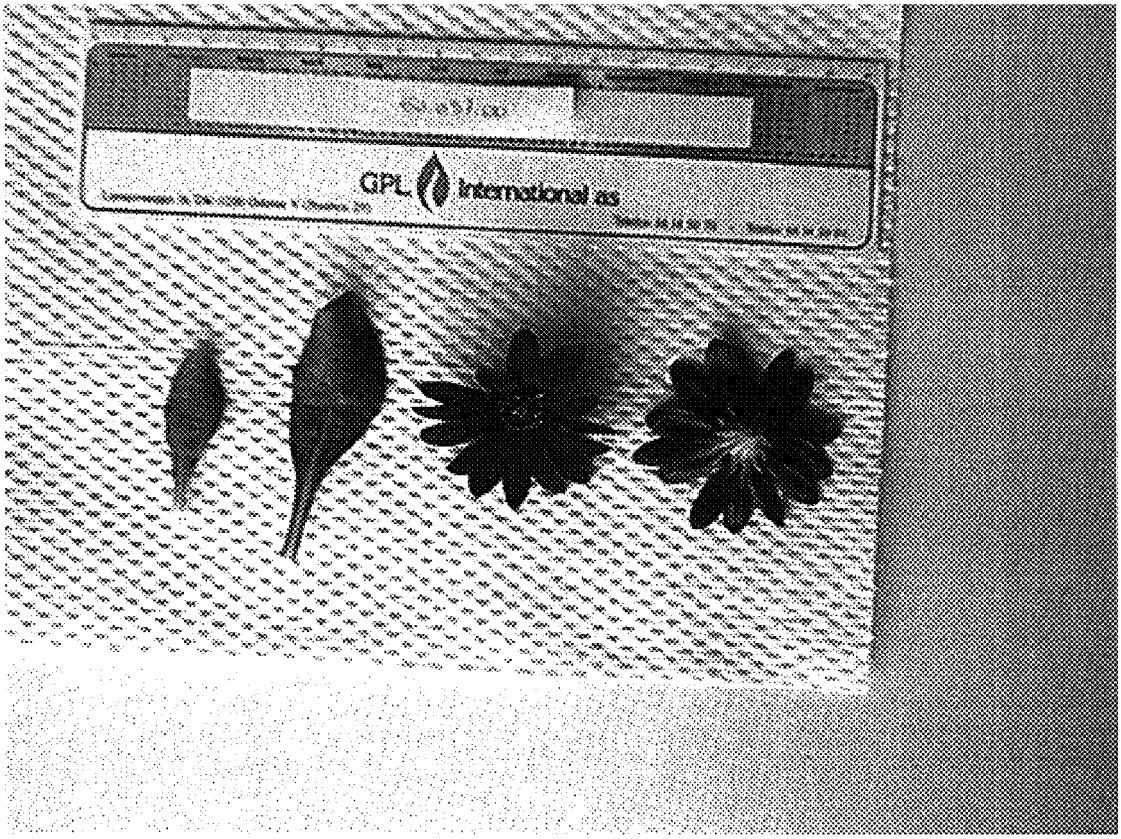
GPL International as